United States Patent [19]

Free

[11] 3,990,434
[45] Nov. 9, 1976

[54] REVERSIBLE INTRAVASAL OCCLUSIVE DEVICE

[75] Inventor: Michael J. Free, Pasco, Wash.

[73] Assignee: The United States of America as represented by the Department of Health, Education and Welfare, Washington, D.C.

[22] Filed: Feb. 18, 1975

[21] Appl. No.: 550,708

[52] U.S. Cl. ............................. 128/1 R; 128/334 C
[51] Int. Cl.² .......................................... A61B 19/00
[58] Field of Search ..................... 128/1 R, 334 C

[56] References Cited
UNITED STATES PATENTS

| | | | |
|---|---|---|---|
| 3,699,957 | 10/1972 | Robinson | 128/1 R |
| 3,704,704 | 12/1972 | Gonzales | 128/1 R |
| 3,820,528 | 6/1974 | Rogers | 128/1 R |
| 3,831,584 | 8/1974 | Bucalo | 128/334 C X |
| 3,877,435 | 4/1975 | Bucalo | 128/334 C |

*Primary Examiner*—Dalton L. Truluck
*Attorney, Agent, or Firm*—Browdy and Neimark

[57] ABSTRACT

A reversible occlusive device for regulating the flow of the fluid through a body passage and having particular utility in the vas deferens for reversible male sterilization is surgically implanted. The vas is punctured by a micro tool such as a hypodermic needle and then a proximal tube having a shoulder portion and openings on either end is inserted. A second hole is punctured in this body passage at a distance approximately equal to twice that of the length of the shoulder portion of the proximal tube. A distal tube similar in construction to the proximal is then inserted into this puncture along with a closed plug for the prevention of the passage of body fluid. If the individual wants the body passage open, the closed plug is surgically removed and is replaced by an open plug.

8 Claims, 3 Drawing Figures

REVERSIBLE INTRAVASAL OCCLUSIVE DEVICE

FIELD OF THE INVENTION

This invention relates to a reversible occlusive device for use in the regulation of the flow of fluid in a body passage. This device is particularly adapted to be used in the vas deferens of the adult male as a means for male sterilization.

BACKGROUND OF THE INVENTION

In recent years, man has become increasingly aware that what was once thought to be a limitless supply of natural and man-made resources has now become alarmingly depleted. This depletion is due in great part to an unparalled increase in the world population. In the first three-quarters of this century, man's growth rate has reached the point whereby he is taking much more out of the world's resources than he has been replacing. If this rate continues, man will reach a point in the near future where he cannot clothe or feed himself properly. To counteract this depletion of resources and to ensure that the necessities of life will be available to everyone, increased encouragement and education has been directed to proper family planning. To accomplish this end, many different devices have been developed to prevent conception, so that the opportunity to make an intelligent decision as to whether two people want and can properly care for a child is available. These devices have been directed toward both the male and the female, but many of them contain serious drawbacks. Several female oral contraceptive devices have been found to cause harmful side effects, and some intra-uterine devices have been linked to cervical cancer.

Vasectomies have gained expanded acceptance in the last few years as a means for preventing pregnancy. However, this method exhibits the serious drawback of being non-reversible. One who has undergone a vasectomy cannot recant on his decision once the operation is completed. Several reversible male sterilization devices have been developed, but these devices have not been very reliable since their construction does not allow the vas to become permanently attached to the device so as to form an intrinsic part of the wall of the device.

SUMMARY OF THE INVENTION

According to the present invention, a plastic, reversible, intravasal, occlusive device has now been developed which can be placed into the vas deferens of the adult male in such a manner that the vas becomes permanently attached to it. This device consists of two tubes and an insert and is used to regulate the passage of the spermatozoa through the vas. Thus, a closed plug insert is used to block the flow of spermatozoa and an open tube insert is used for the restoration of the sperm flow. The placement of the device in the vas and conversion between the open and the closed modes can only be accomplished during a surgical procedure. Due to the particular configuration of the tube, the use of ligatures to maintain the tubes in the vas or the transection of the vas are not necessary with this procedure. This ensures that the vas does not become necrotic, gangrenous and leaky from the pressure of ligatures, nor will the vas wall be irritated or eroded. Furthermore, muscles, blood and lymph vessels and nerves are undisturbed by the utilization of this procedure.

It is, accordingly, an object of the invention to overcome the defects of the prior art as described above.

Another object is to provide an improved manner for the control of conception and pregnancy.

Another object of this invention is to produce a reversible occlusive device which is to be inserted into a body passage.

One other object of this invention is to produce a reversible occlusive device which is inserted into the vas deferens.

Still another object of this invention is to produce a reversible occlusive device whose surface is porous, thereby enabling it to become firmly attached to the vas deferens.

Yet another object of the invention is to produce a reversible occlusive device which requires no ligatures to hold it in place prior to ingrowth.

A further object of the present invention is to produce a reversible occlusive device that does not require the transection of the vas deferens.

Still another object of the invention is to produce a reversible occlusive device which requires surgery to effect the reversal.

BRIEF DESCRIPTION OF THE DRAWING

The above and additional objects and advantages inherent in the present invention will become more apparent by reference to the description of an illustrated embodiment in a drawing thereof in which.

DETAILED DESCRIPTION OF PREFERRED EMBODIMENTS

Figure 1:
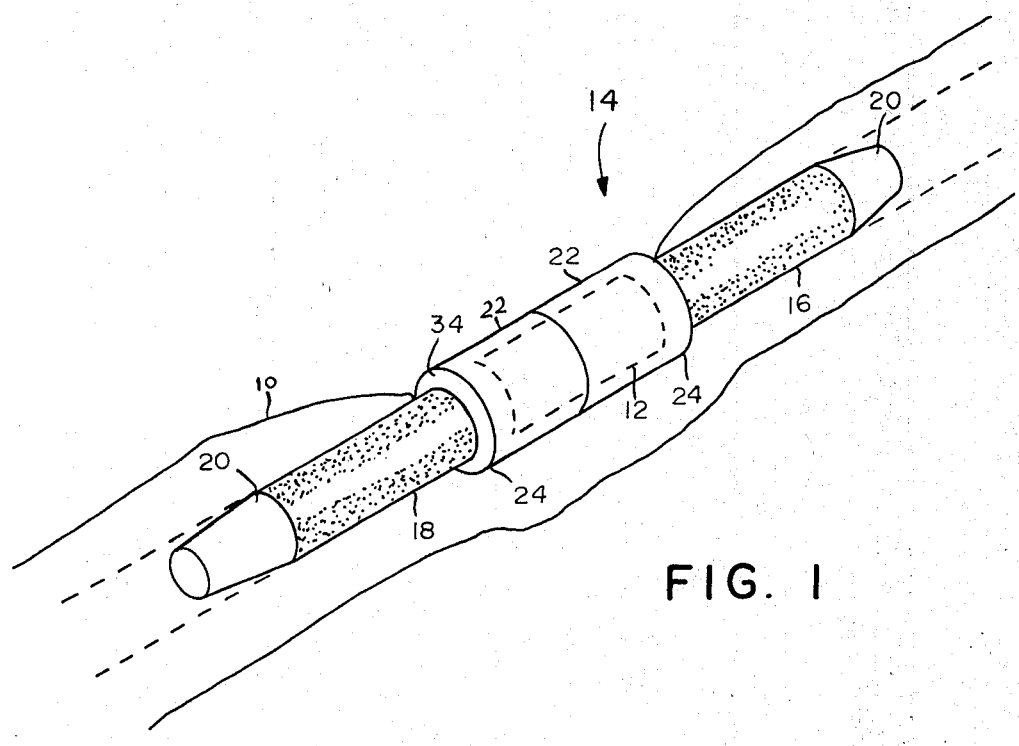
FIG. 1 is a perspective view of an embodiment of an occlusive device of the present invention.

FIG. 1 shows an occlusive device 14 inserted into a body passage 10 such as the vas deferens. The device 14 is composed of a proximal tube 16, a distal tube 18 and one of either of two inserts 12, one of which is hollow and the other of which is solid. To facilitate the insertion of the two tubes into the vas deferens, the ends of each of the tubes are tapered at 20.

The prevention of migration of the reversible occlusive device 14 after it has been inserted into the vas deferens 10, which is of prime importance, is accomplished by providing shoulders 22 on the untapered ends of the tubes 16 and 18. These shoulders 22 have abruptly terminating ends 24 whose surfaces 34 are substantially perpendicular to the tubes 16 and 18. In addition, each of the tubes 16 and 18 has an outer surface provided with irregular pores 32 (see FIG. 3) with a diameter of between 10 and 200 microns. These pores allow the ingrowth of connective tissues which occurs within a few days of installation and which effectively anchors and seals the device in the vas. This device should be constructed of inert and non-toxic polymeric materials throughout such as polyurethane, soft grades of ethylene/vinyl acetate polymer, polyethylene, ethylene-propylene rubber, silicone rubber or other inert and non-toxic flexible plastic. This type of material is compliant enough to respond to tissue and muscle deformation.

Depending upon the material from which the tubing 16 and 18 is formulated, different methods may be used to provide the pores on the outer surface. For example, if the distal and proximal tubes are constructed of ethylene/vinyl acetate polymer, the pores will be produced by slowly spinning the tubes on a spring mandrel while sanding it with an appropriate grade of sandpaper, such as 80 grit flint paper.

Figure 2:
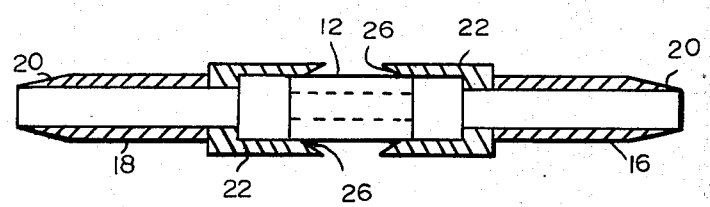
FIG. 2 is a cross-sectional view taken through line 1—1 of FIG. 1 prior to pushing the tubes together.

FIG. 2 shows a cross-sectional view of the occlusive device 14 in its open mode immediately prior to pushing the tubes together, it being understood that in the closed mode the hollow insert 12 is replaced with a solid insert. The shoulders 22 are provided with an inside taper 26 to assist in fitting the tubes 16 and 18 over the plug 12.

In the preferred embodiments, the shoulder has an outer diameter of approximately 0.07 inches. Each of the tubes is approximately 0.3 inches long with the plug being about 0.15 inches long. The outer diameter of the tubes is about 0.03 inches and the inner diameter is approximately 0.02 inches.

Figure 3:
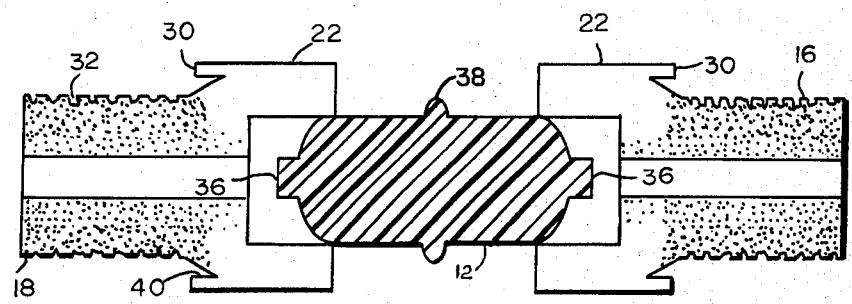
FIG. 3 is a longitudinal cross-section of another embodiment of a device of the present invention.

FIG. 3 shows another embodiment of this device in its closed mode just before the proximal and distal tubes are pushed towards one another. In this variation, the shoulders 22 are provided with an angular annular lip 30 in the direction away from the plug 12, thus forming an annular slot 40 between the tubes 16 and 18 and the shoulders 22. This configuration serves the same purpose as the abruptly terminating ends 24 of the FIG. 1 embodiment by preventing the migration of the device until overgrowth and ingrowth of connective tissues can occur. A pair of projections 36 are provided on the ends of the closed plug 12 to fit snuggly into the passages in the proximal and distal tubes 16 and 18. In the center of and completely encircling the plug 12 is a collar 38 which is employed to ensure that a tight fit is maintained between the two tubes 16 and 18.

The device is inserted into the vas deferens in three stages. Each tube 16 and 18 is placed onto a snug fitting mandrel, the free end of which protrudes a few millimeters beyond the tip 20 when the free end of the shoulder 22 is abutting against the hub of the mandrel. The vas is then punctured with a tapered micro-tool such as a hypodermic needle which is directed toward the testis. The mucosa of the vas in the insulation segment can be destroyed at this time, using for example, a bipolar electrocautery, a reaming instrument or schlerosing agents. The free end of the mandrel carrying the tube is then inserted into the hole and the mandrel and the proximal tube 16 are pushed into the vas. The mandrel is then removed leaving the proximal tube in place.

A second puncture is made in the vas at the same point on the circumference as the previous hole and at a distance from the first hole equal to the length of the two shoulder portions 22. The distal tube 18 is now inserted through this hole in the direction of the body in a similar fashion to the first half. A closed plug 12 is inserted into the proximal tube and the distal tube is pushed over the other end of the plug.

If the individual wishes that the device be operated in the open mode, the closed plug insert is surgically replaced by an open one. An incision is made in the vasal sheath exposing the shoulders 22 of the reversible occlusive device. The two ends of the tubes 16 and 18 are pulled off the plug insert 12 and an open insert is replaced in a manner similar to the placement of the closed plug. To facilitate the recognition of which mode this device is operating, a color coding may be used. For example, the open mode insert may be white and the closed mode plug may be black.

The fact that the reversal in modes can only be made surgically is of great advantage in this particular device since the decision to operate is never made lightly. This device is also better to prevent impregnation since the closed plug cannot come loose and it is impossible for spermatozoa to pass through the device.

While this device has been described with particular reference to its use in the vas deferens, it should not be construed to be so limited and may be utilized in many different body passages. It will be obvious to those skilled in the art that various changes may be made without departing from the scope of the invention and the invention is not to be considered limited to what is shown in the drawings and described in the specification.

I claim:

1. A reversible occlusive device for regulating the flow of fluid in a body passage defined by a duct and which permits insertion into the duct without severing the duct into two pieces, said device being free of any duct-clamping members and consisting of:
   means free of external clamping surfaces for insertion into a body passage without severing the duct into two pieces, said means comprising a proximal tube and a distal tube, each of said tubes having a foward and back end, said tubes being of relatively constant exterior diameter throughout a substantial portion of their lengths and adapted for placement end to end in the unsevered duct, being formed of soft, inert and non-toxic plastic and having a roughened or porous surface;
   means free of clamping surfaces for abutting the duct including first and second shoulder means each having a forward and back end, said first shoulder means circumferentially surrounding the forward end of said proximal tube and said second shoulder means circumferentially surrounding the forward end of said distal tube for the prevention of the migration of the occlusive device in the unsevered duct, whereby the duct abuts the back end of each of said shoulder means, said back end of each of said shoulder means being at least partially substantially perpendicular to said tubes; and
   regulating means connected between said proximal and distal tubes for the regulation of the flow of a fluid in a duct;
   whereby when said regulating means is closed, the fluid ceases to flow in the duct and when said regulating means is open, the fluid is allowed to pass.

2. The device according to claim 1, wherein said regulating means is open.

3. The device according to claim 1, wherein said regulating means is closed.

4. A device according to claim 1, wherein said back end of each of said shoulder means includes an inclined surface and an annular lip so that an annular slot is formed between said lip and said tubes.

5. A device according to claim 1, wherein both said proximal and said distal tubes are tapered in the direction toward their back ends.

6. A device according to claim 1, wherein said regulating means and said proximal and distal tubes are constructed of polyurethane or soft grades of ethylene/vinyl acetate polymer.

7. A method for the insertion of a reversible occlusive device for regulating the flow of fluid in a body passage defined by a duct, the method comprising the steps of:

exposing a portion of said duct by making an incision;
puncturing said portion of said duct without severing same to provide a first puncture;
inserting a proximal tube having a shoulder into said duct at said first puncture to a distance where said shoulder abuts said duct;
puncturing said duct at a distance from said first puncture approximately equal to twice the length of said shoulder without severing said duct to provide a second puncture;
inserting a distal tube having a shoulder into said duct at said second puncture to a distance where its shoulder abuts said duct;
inserting one end of a closed regulating plug into said proximal tube;
pushing said distal tube over the second end of said regulating plug; and
closing said incision without first clamping the duct to either of the tubes.

8. A method according to claim 7, further including the steps of:
removing said closed regulating plug; and
inserting an open regulating plug in its place.

* * * * *